US007831408B2

(12) United States Patent  
Petrucelli

(10) Patent No.: US 7,831,408 B2  
(45) Date of Patent: Nov. 9, 2010

(54) DEVICE FOR DETECTING AND DISPLAYING ONE OR MORE OF BODY WEIGHT, BODY FAT PERCENTAGE, BLOOD PRESSURE, PULSE AND ENVIRONMENTAL TEMPERATURE

(75) Inventor: Steven Petrucelli, Cranbury, NJ (US)

(73) Assignee: Measurement Ltd., Grand Cayman (KY)

( * ) Notice: Subject to any disclaimer, the term of this patent is extended or adjusted under 35 U.S.C. 154(b) by 200 days.

(21) Appl. No.: 11/985,345

(22) Filed: Nov. 14, 2007

(65) Prior Publication Data

US 2008/0183398 A1 Jul. 31, 2008

Related U.S. Application Data

(60) Provisional application No. 60/859,221, filed on Nov. 15, 2006.

(51) Int. Cl.
*G07G 7/00* (2006.01)
*G01K 13/00* (2006.01)

(52) U.S. Cl. .................. 702/173; 702/130; 702/131; 702/132

(58) Field of Classification Search ............... 702/104, 702/130–132, 173, 188–190; 324/692
See application file for complete search history.

(56) References Cited

U.S. PATENT DOCUMENTS

| 2002/0183646 A1* | 12/2002 | Stivoric et al. | 600/549 |
| 2003/0023186 A1* | 1/2003 | Ueda et al. | 600/547 |
| 2004/0196054 A9* | 10/2004 | Liu et al. | 324/692 |
| 2008/0004904 A1* | 1/2008 | Tran | 705/2 |

\* cited by examiner

*Primary Examiner*—Hal D Wachsman
*Assistant Examiner*—Phuong Huynh
(74) *Attorney, Agent, or Firm*—Howard IP Law Group, PC

(57) ABSTRACT

A device for measuring and displaying body parameters includes a sensor that generates a signal representing a detected body parameter, such as body fat, body water and weight, and blood pressure of an individual; a transmitter to wirelessly transmit the signal; a receiver to receiver and display the sensed measurements as well as a user's name, time, date and temperature. The invention also pertains a method for determining fitness comprising the steps of: inputting, data pertaining to one of date, time, an individual's name, and fitness statistics, sensing parameters of one or more of a body fat, a body water, blood pressure and a weight; recording sensed parameters and said data; and transmitting the sensed parameters and said data; receiving said sensed parameters and said data and a signal proportional to a temperature and displaying one or more of said sensed parameters, data and temperature on a portable display unit.

6 Claims, 5 Drawing Sheets

DEVICE FOR DETECTING AND DISPLAYING ONE OR MORE OF BODY WEIGHT, BODY FAT PERCENTAGE, BLOOD PRESSURE, PULSE AND ENVIRONMENTAL TEMPERATURE

CROSS REFERENCE TO RELATED APPLICATION

This application claims priority of U.S. Patent Application Ser. No. 60/859,221, entitled WEIGHING SCALE, filed Nov. 15, 2006, the entire disclosure of which is hereby incorporated by reference as if being set forth in its entirety herein.

FIELD OF THE INVENTION

This application relates generally to weighing scales and to body sensors.

BACKGROUND OF THE INVENTION

Bathroom scales for measuring body fat and weight are known apparatuses used by the general public and particularly individuals that are fitness conscious. Weight alone does not provide an accurate assessment of an individual's fitness or progress in attaining fitness. For fitness conscious individuals, body fat measurements, in addition to body weight, may improve their assessment of their progress toward reaching, and their diligence in maintaining, fitness goals. Accuracy and reliability depend to some degree on using the same measurement devices. However, the prior art lacks a low cost device that will accurately monitor several bodily parameters over time that also uses the same technique to observe and record associated changes in parameters such as body fat, weight and body water percentage. Additionally, in order to make body fat and body water percentage or water readings are more accurate, it is helpful to have a general category of "fitness level". Although the prior art deals with one or another aspect of fitness, none deals with the capability of having a broad range of salient statistics available in the scale and in a hand held device that can be up-dated to suit individual users.

Electronic blood pressure measuring devices typically automatically apply pressure via a pump to inflate the arm cuff. The inflation pump contains a one-way valve to prevent inadvertent pressure leaks while other mechanisms allow the pressure in the system to drop in a controlled manner. In the typical mode of operation, the cuff is placed around part of the arm. In some applications the cuff is placed approximately one-half inch above the elbow at roughly the same vertical height as the heart while the individual is in an upright position. In other devices the cuff may be placed around the wrist. The cuff is inflated until the artery within the arm is blocked off. Once the blood flow is blocked cuff pressure is gradually decreased using electrically controlled valves. As the pressure in the cuff diminishes, blood begins to flow through the previously blocked off artery. As indicated in the prior art sounds of the blood initially flowing at or near the time the initial deflation occurs and later, when blood flow resumes its normal state blood pressure is determined. The pressure sensed at the onset of blood flow is referred to as the systolic blood pressure. As cuff pressure continues to decrease a steady state pressure is reached and is referred to as the diastolic blood pressure. In certain conventional electronic blood pressure monitors blood pressure is calculated according relationships between average and peak widths of a pulsed wave detected when the cuff is pressurized and depressurized. The prior art digital blood pressure meters use determine blood pressure and register the data on a digital read out. These read outs are integrally connected to the meters which are not practicably portable.

SUMMARY OF THE INVENTION

According to an aspect of the present invention, a weighing scale utilizes a body fat sensor, a body water sensor and a weight sensor coupled to a processor having therein contained a program to record fitness level, display the sensed parameters and transmit the parameters to a portable display unit. The combined sets of readings comprise a statistical set that may be combined to produce a level of fitness for individual users. The weighing scale also includes a "weight only" function that allows the body fat scale to also be used as a typical bathroom scale.

In yet another embodiment a device measures body fat and body water percentages, and tracks weight to show the individuals target or goal weight and the difference between the goal and the current weight.

In one embodiment a wireless display unit is attachable and detachable from the scale. When the display unit is removed from the scale it can be hand held or placed on a wall or flat surface. An exclusive remote sensor reads the outside temperature and time, which is transmitted to the scale periodically and displayed when the scale or the portable unit is not being used. The scale and the display unit contain memory devices to record and store statistical information such as time, date and an identifier related to personal data such as the individual's name, and the associated fitness statistics received. In yet another embodiment, the scale and the display device include corresponding pass codes to protect the personal data of a particular user and to authenticate the identity of the user.

The invention disclosed herein also includes a method for utilizing a body fat sensor, body water sensor and a weight sensor coupled to a processor having therein contained a program to record a fitness level: providing a scale for individuals to obtain measurements for one or more of an individual's body fat, body water and weight; generating one or more output signals proportional to the one or more of body fat measurement, body water measurement and weight measurement; and transmitting the one or more outputs to a receiver for displaying the measurements.

According to an aspect of the present invention, a blood pressure monitor generates an output signal proportional to the systolic blood pressure and the diastolic blood pressure and transmits the signal to a remote receiver that includes a processor and memory code operable calculate and to record blood pressure and pulse, and other statistical information such as time, date and an identifier related to the user's name and indicative of a level of wellness for individual users.

In yet another embodiment a blood pressure or pulse rate system comprises one or more blood pressure or pulse rate meters, each having a plurality of sensors that generate a plurality of output signals proportional to one or more of a sensed blood pressure, pulse rate and a means to sense temperature; each sensor having a means to communicate to one or more associated portable display units; each said portable display unit including a means to receive and a processor code operable to calculate a measure of blood pressure or pulse rate based upon the output signal data and input data pertaining to vital statistics of each user; and displaying the blood pressure, pulse rate and temperature.

In yet another embodiment, the remote device includes corresponding pass codes to protect the personal data of a particular user and to authenticate the identity of the user. A remote sensor also reads the outside temperature and time, which is transmitted a wireless remote unit to periodically display the temperature and time when the portable unit is not being used to record blood pressure or pulse rate.

DETAILED DESCRIPTION OF THE INVENTION

In the figures to be discussed, the circuits and associated blocks and arrows represent functions of the process according to the present invention, which may be implemented as electrical circuits and associated wires or data busses, which transport electrical signals. Alternatively, one or more associated arrows may represent communication (e.g., data flow) between software routines, particularly when the present method or apparatus of the present invention is a digital process.

Figure 1:
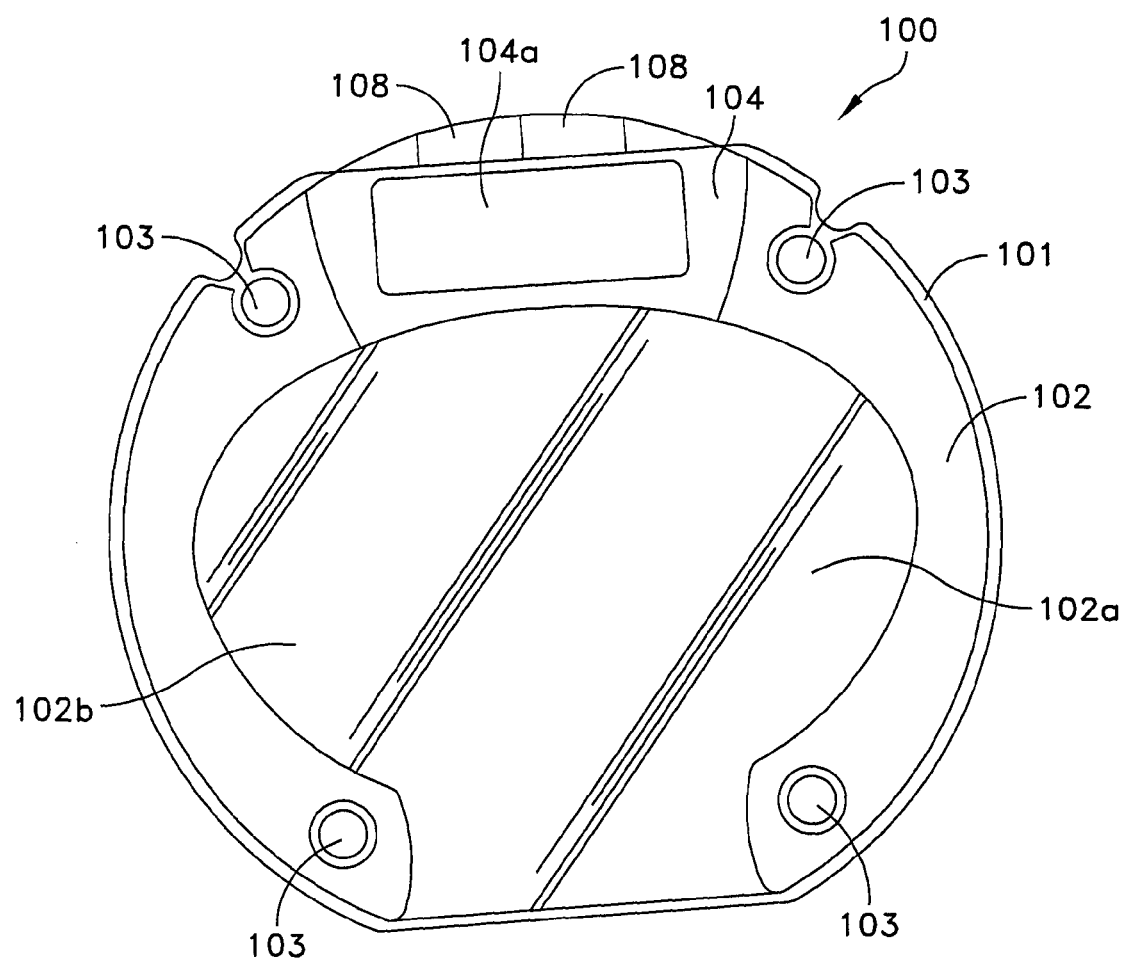
FIG. 1 illustrates an apparatus for detecting and displaying one or more body parameters in accordance with an embodiment of the present invention.

Referring to FIG. 1, there is illustrated an apparatus 100 for detecting and displaying one or more body parameters and other information. Apparatus 100 includes scale 101 having sensors for determining body fat, body water percentage and weight, portable display unit 104, temperature sensing unit 105 (of FIG. 2), and blood pressure unit 106 (of FIG. 2). Scale 100 includes a platform 102, which is transparent in the illustrated embodiment, which supports an individual who desires to be weighed. Platform 102 rests on load cells 103, which in turn are supported on the body of scale 101. Scale 101 also includes circuits (not shown) which may be operated to measure body fat and body water percentage. Such circuits and associated data processing software are well known to those of skill in the art. By way of non-limiting example, electrodes 102a, 102b, which may be transparent, may contact the body to provide a generated electrical current to the body. The electrical current passes more easily through lean muscle than fat, and cell water percentage levels affect the resistance and the reactance of the impedance measured. The prior art discloses a body composition determined from a calculation based upon the speed at which the signal passes through the body. The values for resistance and reactance, the subject's height and weight all serve as inputs to well-known equations in algorithmic form as embodied in a computer programs to yield body composition measurements such as body mass index (BMI), a measure of body fat based on height and weight that applies to both adult men and women. Such programs are known in the published art.

Portable display unit 104 is removable from scale 101, and may be housed, as illustrated in FIG. 1, in a recess defined in scale 101. Portable display unit 104 includes a display 104a, which displays information received from scale 100, such as body fat, body water percentage and weight, and temperature information received from temperature sensing unit 105 (of FIG. 2). Portable display unit 104 may be held in the hand, mounted on a wall or other convenient location for viewing, or positioned in the housing of scale 101. In one embodiment, scale 101 includes a wireless transmitter, such as a wireless radiofrequency transmitter, and portable display unit 104 includes a wireless radiofrequency receiver. Temperature sensing unit 105 (of FIG. 2) may also include a wireless radiofrequency transmitter. Temperature sensing unit 105 (of FIG. 2) may be mounted in an area where it is desirable to obtain a temperature reading, such as a location outdoors. Portable display unit 104 includes a means to receive, transmit and store data pertaining to keyed input, body fat, body water, weight and outside temperature. Portable display unit 104 also includes key input switches 108 for optionally inputting various parameters such as an individual's name, time, target weight, and other personal data as described below.

Figure 2:
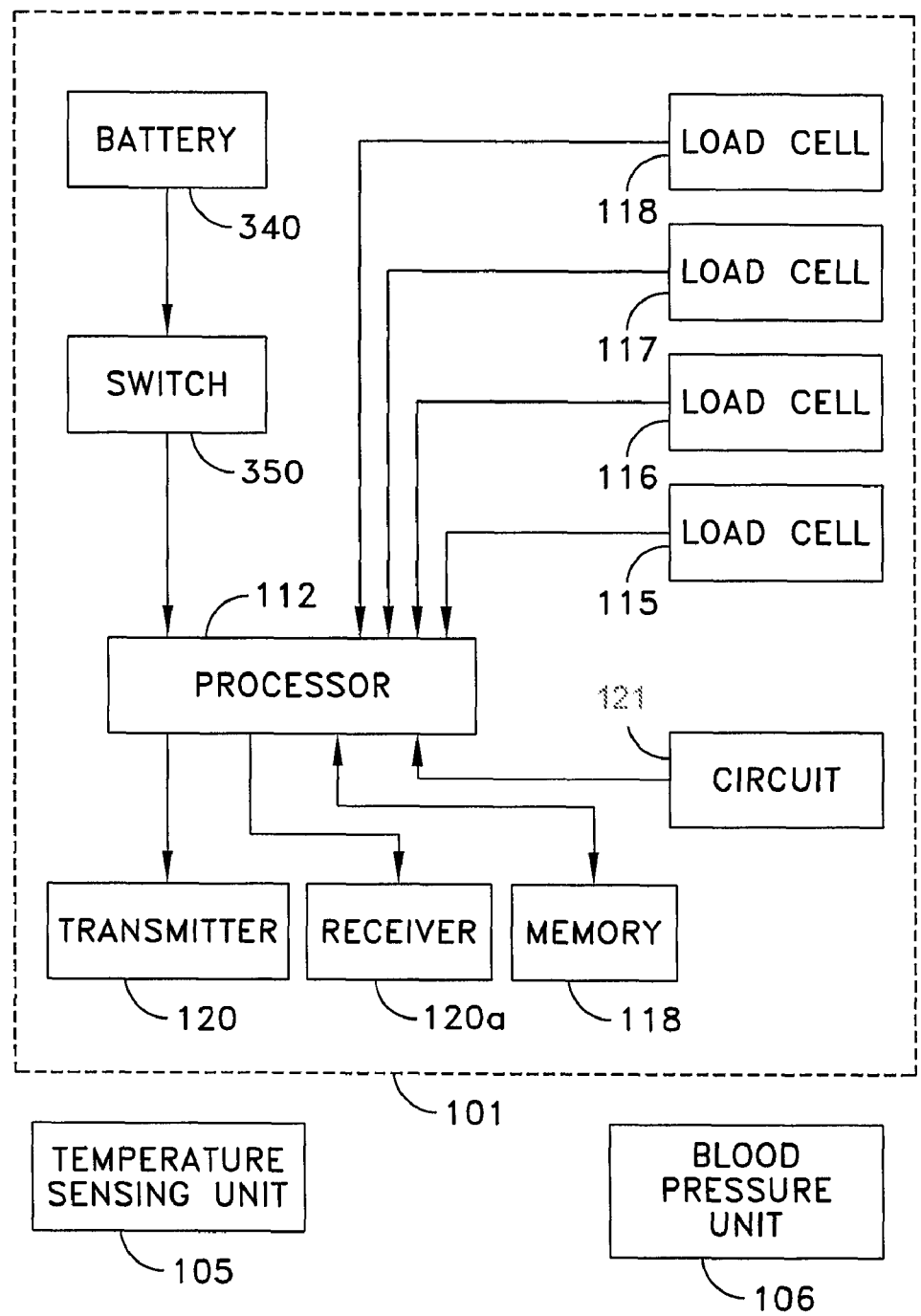
FIG. 2 is a block diagram of a scale in the apparatus of FIG. 1.

As illustrated schematically in FIG. 2, scale 101 includes processor 112 having memory 118. Processor 112 is coupled to sensors, including load sensors 115, 116, 117 and 118. Such load sensors may be positioned so as to support platform 102 shown in FIG. 1. Processor 112 is also coupled to circuit 121, which is coupled to electrodes 102a, 102b shown in FIG. 1. An output of circuit 121 may be interpreted by suitable programming to provide an output proportional to the body fat percentage or the body water percentage of a person having body parts in appropriate contact with electrodes 102a, 102b.

Processor 112 is also coupled to wireless transmitter 120.

Figure 3:
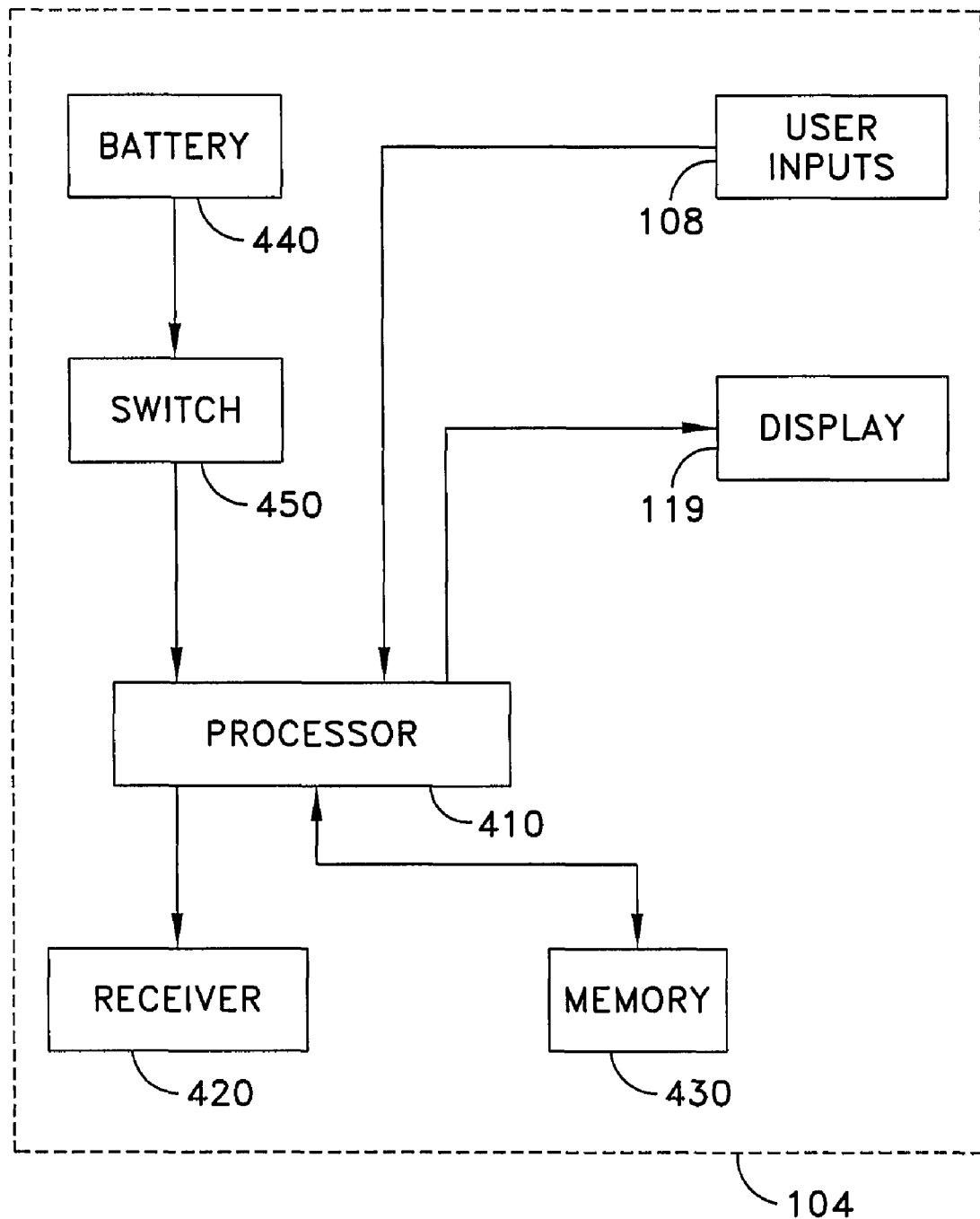
FIG. 3 is a block diagram of a base unit of the apparatus of FIG. 1.

Referring to FIG. 3, portable display unit 104 will now be discussed. Portable display unit 104 includes a processor 410, memory 430, power supply 440, display 119, user inputs 108, and wireless receiver 420. Processor 410 may be programmed to cause display 119 to display data received via wireless receiver 420.

Each of scale 101, temperature sensing unit 105, and blood pressure unit 106 may include a processor, memory, and wireless transmitter. Readings obtained from any of these units may be wirelessly transmitted to receiver 420 of FIG. 3. Temperature sensing unit 105 may provide a reading of temperature in an environment, such as an outdoor environment. Scale 101 may also contain a receiver 120a, optionally.

Figure 4:
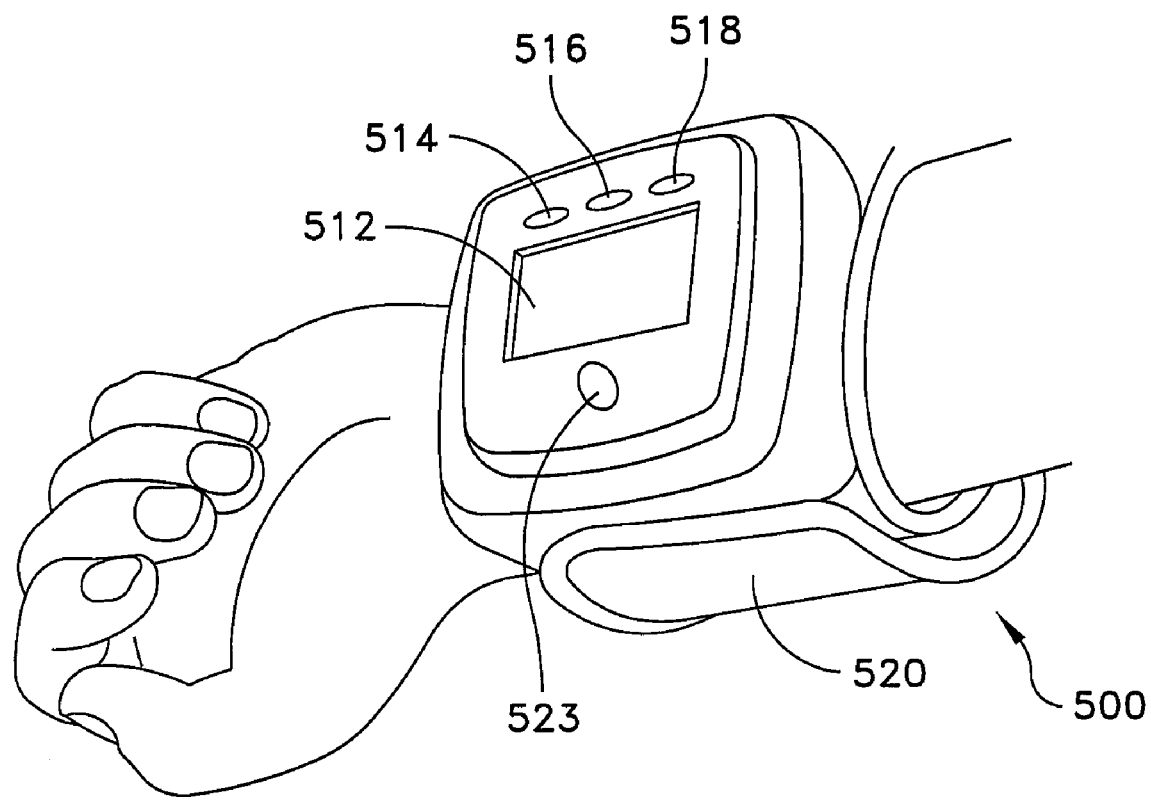
FIG. 4 is a view of an apparatus for measuring blood pressure and pulse rate in accordance with an embodiment of the present invention.
Figure 5:
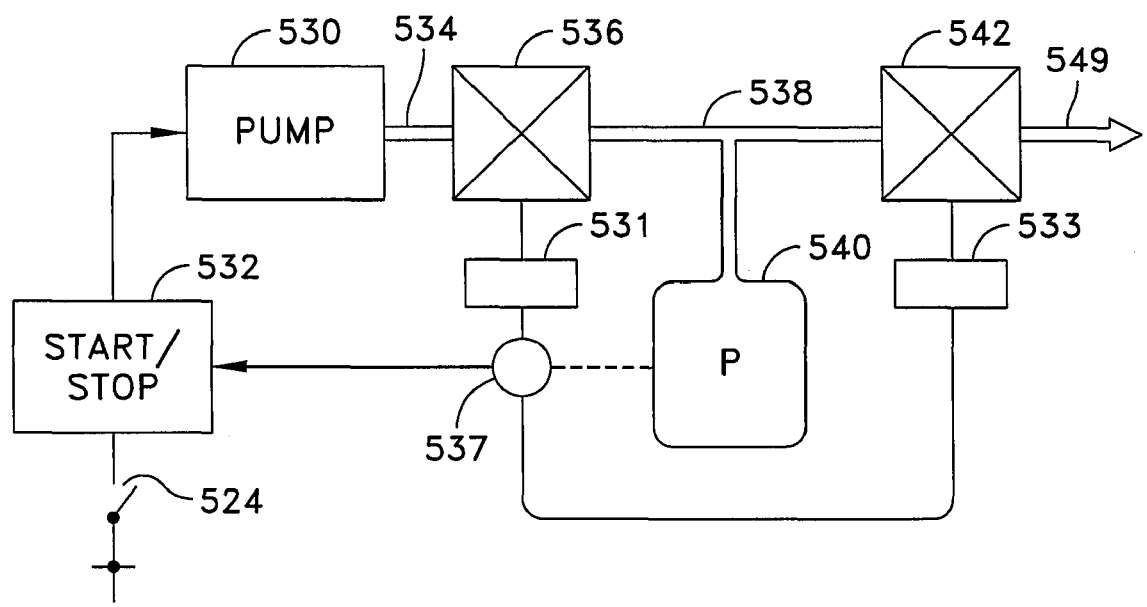
FIG. 5 is a schematic diagram illustrating an apparatus for measuring blood pressure and pulse rate.

Referring now to FIG. 4, there is shown a blood pressure measurement unit 500. Blood pressure measurement unit 500 detects blood pressure measurements and pulse rate information, and provides an output signal, which may be wirelessly transmitted and received and displayed by portable display unit 104 (of FIG. 1). Blood pressure measurement unit 500 is affixed to armband 520. Armband 520 may be secured to an individual's arm, such as at the wrist or upper arm, as illustrated generally in FIG. 4. Blood pressure measurement unit 500 may include a local display unit 512 to display the detected blood pressure readings and pulse rate. Referring to FIG. 5, start/stop circuit 532 is connected to a user input, such as a button or touchpad, 523. Start/stop circuit 532 is operably connected to switch 524, which, when closed, such as by pressing a button, causes pump 530 to be connected to a power supply. Pump 530 inflates armband bladder 540. Upon inflation, a suitable pressure is applied by the bladder to the individual's arm. Pressure sensors provide a signal indicating the detected pressure to the processor. The processor provides data to the local display 512, so that the detected pressure and pulse rate are displayed. The pulse rate may be calculated based on variation in pressure readings, as is well known in the field. The processor also provides the data to a wireless transmitter. The data may be received by receiver 420 of FIG. 3, and then sent by processor 410 of the base unit 104 to display 119 of the base unit.

Switch 24 in association with the start/stop circuit causes pump 530 to pump air via line 534 through check valve 536 and through line 538 to inflate bladder 540. Sensor 537 is in contact with a surface of bladder 540 and senses pressure P. A reading from sensor 537 may be provided to a processor, as explained above, which may provide a signal to disable pump 530. Such signal may, by way of example, turn off start/stop circuit 532 stopping the pump 530 or causing electronic solenoid 531 to disable check valve 536 when the pressure P reaches a designed pressure, such as approximately 195 mm HG. Under the pressure P of inflated arm band bladder 540, an arm is constricted and blood flow through arm in the area where apparatus 500 is mounted is reduced or cut off. Having attained the proper level of applied arm pressure P, valve 542 under control of valve controller 533 housed in apparatus 500 slowly allows pressure P in armband bladder 540 to dissipate or exhaust air through port 549. As the blood is allowed to resume flow, sensor 50 detects the higher systolic blood pressure and the lower diastolic blood pressure. The two sensed blood pressure readings serve as input to a processor, which then provides the data to display 512, so as to display the two pressures as systolic blood pressure 518 and diastolic blood pressure 516, as seen in FIG. 4.

In addition to sensing systolic blood pressure and diastolic blood pressure, apparatus 500 also detects the pulse rate 514. A pressure sensor, which may be in a position to be in contact with the person's arm, provides a continuous or periodic pressure signal to a processor, which analyzes and determines a pulse rate 514 based on the varying pressure signal received. The processor outputs the pulse rate 514 to display 512, and may also cause the pulse rate 514 to be wireless transmitted for reception at base unit 104. An additional sensor, which may read, for example, skin temperature, may also be provided. The optionally sensed input serves as input to processor 70, which processes code that formats and outputs the optionally sensed data to display 12.

Referring again to FIG. 3, processor 112 is also coupled to user inputs 108. One such input to the processor 112 is to receive via key 108 data in response to prompts generated on the display by processor 112 executing one or more programs stored in memory. Processor 112 may prompt the user for, and receive, via inputs at key 108, such parameters as time, user identities, target weight, user age, and other personal data of the user.

As will be apparent from the foregoing a designer of a system incorporating the scale, temperature unit, blood pressure unit, and the portable display 104, needs to decide where to include certain functions as performed by the combination of the two devices. For example, when the portable unit 104 is installed in the scale 101, a single processor may serve the roles of both processor 112 and processor 410. If the portable display unit 104 has been detached from the scale 101, the scale 101 must include a means for transmitting the sensor data to the display unit 104. Therefore, where to accomplish the processing of the sensor data, input data related to fitness statistics and temperature is a design choice.

Returning to the scale 101 that includes a processor 112, the processor is generally a microprocessor that includes a memory 118 for storing one or more measurements including inputs from load cells and body fat sensors, and may also store outside temperature and key data from unit 104 and statistical information such as time, date and an identifier for related to the user's name. The processor 112 permits settings related to receiving input sensor data, storing the data, retrieving the data and other information such as the statistics recorded in memory 118 and communicating with display unit 104 and alternatively transceiver 110. The reference to transceiver refers to any device capable of transmitting and/or receiving. Whether the receiver and transmitters are integrated or not is a design choice and does not alter the intents supporting the invention herein.

In some embodiments, outside temperature is sensed by a thermometer which has an associated transmitter that periodically communicates the outside temperature the receiver of base unit 104, which is then received by the processor, which then displays, and may store, the temperature. Upon receiving the information related to one or more of the body fat measure, body water measure and weight measure as determined from the scale 101, the processor 410 may cause this data to be stored, such as in memory 430. Memory 410 may include stored measurements including statistical information such as time, date, outside temperature, an identifier related to the user's name, age, height and the associated weight, body fat and body water percentage received. The key input 108 interfaces with the processor 410 to permit settings related to storing weights, retrieving information such as the statistics recorded in memory 180 and displaying the statistics.

According to an aspect of the present invention, a wired connection may be provided between scale 101 and base unit 104, when base unit 104 is located in scale 101, as shown in FIG. 1. Alternatively, wireless communication may be used at all times. The communication protocol utilized in embodiments of the invention may be way of non-limiting example be described as follows: (1) upon sensing that an individual has mounted the scale, processor 112 initiates a request to the unit 104 to determine if the unit is attached to the scale 101. If the unit 104 has not been detached then all further communication regarding the body fat measure, body water measure and weight measure as determined from the scale 101 inputs is sent to unit 104 by a wired connection. (2) If processor 112 determines that unit 104 has been detached then processor 112 employs wireless communication. In a first communication processor 112 initiates a request to the user via transceiver that the user identify itself via unit 104. Thereafter a second communication from transceiver 110 sends information related to one or more of the body fat measure, body water measure and weight measure as determined from the scale 101 inputs through the transmission channel initiated by transceiver 110 and the particular unit 104 that responded to the processor 112 inquiry. The communication protocol utilized by transceiver 110 and the transceiver 165 combinations may be way of by way of non-limiting example, a Wi-Fi-enabled computer and/or handset that uses radio technologies based on as for example the IEEE 802.11 standard to send and receive data anywhere within the range of a base station transceiver or a Bluetooth® wireless technology transceiver. Information from the scale 101 is communicated to the portable device 104 that may, for example, take the form of a hand held display such as removable display unit 104 or may be configured to communicate with a personal digital assistant (PDA), such as a handheld mobile phone, BlackBerry® wireless platform or similar device. The application software installed in the device 104, may by way of non-limiting example employ Physical Markup Language (PML). PML, a markup language based on XML for communicating a description of physical environments and the objects within them, their relationships to the user of the product associated with as in this instance a transmitter of weight information, and the space or location where the scale 101 may be located.

The invention herein is not limited to a single receiver in the base unit, but may include communications with one or more receivers depending on the particular application. For non-limiting purposes of explanation, in one embodiment the transmitter 150 communicates with the transceiver 165 within the associated display unit 104 up to sixty (30') feet from the point of measurement.

In an alternate embodiment the invention the portable unit 104 may receive communication from one or more scales 101 distributed at different locations. The convenience factor is that an individual may carry the portable unit 104 from place to place and have the benefit of determining fitness if a scale 101 were available. The user may by way of non-limiting example, install the portable unit 104 into the scale 101 and proceed to make the measurements as previously indicated. Alternatively, the user may choose to keep the portable unit 104 removed from the scale 101, and make the measurements as previously indicated, in which case the scale 101 would transmit the measurements to the portable unit 104. In this application the scale system 100 comprises one or more scales 101, each having load cells and units for determining body fat, body water percentage, and/or temperature. Each may have a transmitter for communicating the output signals to one or more associated portable display units 104; each said portable display unit 104 including a means to receive and a processor to calculate a measure of fitness based upon the output signals and inputs pertaining to vital statistics of each user; and displaying the output signals and inputs.

Those skilled in the art of computer programming will appreciate that the invention may be implemented in a system of computer units or processors communicatively coupled to one another over a network, such as a wide area network. "Processor", as used herein, refers generally to a computing device such as a microprocessor having a CPU. A CPU generally includes an arithmetic logic unit (ALU), which performs arithmetic and logical operations, and a control unit, which extracts instructions (e.g., code) from memory and decodes and executes them, calling on the ALU when necessary. "Memory", as used herein, refers to one or more devices capable of storing data, such as in the form of chips, tapes, disks or drives. Memory may take the form of one or more random-access memory (RAM), read-only memory (ROM), programmable read-only memory (PROM), erasable programmable read-only memory (EPROM), or electrically erasable programmable read-only memory (EEPROM) chips, by way of further non-limiting example only. Memory may be internal or external to an integrated unit including a processor. Memory may be internal or external to an integrated unit including a personal computer. Memory unit preferably stores a computer program, e.g., sequence of instructions being operable by the processor.

The invention herein also includes a method for weighing comprising the steps of: providing a scale for individuals to obtain measurements for one or more of an individual's body fat, body water and weight; generating one or more output signals proportional to the one or more of body fat measurement, body water measurement and weight measurement; and transmitting the one or more outputs and receiving the outputs and displaying the measurements.

The invention herein also includes a method of inputting, data pertaining to one of date, time, an individual's name, and fitness statistics, sensing parameters of one or more of a body fat, body water and weight; recording the sensed parameters and said data; and transmitting the sensed parameters and said data; receiving said sensed parameters and said data and a signal proportional to a temperature and displaying one or more of said sensed parameters, data and temperature on the portable display unit.

While the present invention has been described with reference to the illustrative embodiments, this description is not intended to be construed in a limiting sense. Various modifications of the illustrative embodiments, as well as other embodiments of the invention, will be apparent to those skilled in the art on reference to this description. It is expressly intended that all combinations of those elements that perform substantially the same function in substantially the same way to achieve the same results are within the scope of the invention. Substitutions of elements from one described embodiment to another are also fully intended and contemplated.

What is claimed is:

1. A system for detecting and displaying one or more of body weight, body fat percentage, blood pressure, pulse and environmental temperature comprising:
   a weighing scale comprising:
      a body fat sensor for generating an output proportional to body fat of an individual;
      a body water sensor for generating an output proportional to body water of the individual;
      a weight sensor for generating an output proportional to weight of the individual;
      a first wireless transmitter adapted to transmit data indicative of said outputs of said body fat sensor, body water sensor and weight sensor;
   a processor coupled to said body, body water, and weight sensors;
   a remote temperature unit for detecting an outdoor temperature and comprising a second wireless transmitter for transmitting data indicative of the outdoor temperature; and
   a blood pressure unit comprising a third wireless transmitter; and
   a portable display unit adapted to be attachable and detachable from said weighing scale and adapted to be housed in a recess defined in said weighing scale, said portable display unit comprising a wireless receiver adapted to be in wireless communication with said first, second, and third wireless transmitters, said display unit adapted to display said data transmitted by said first, second, and third transmitters and received by said wireless receiver.

2. The system of claim 1, wherein said blood pressure unit further comprises a skin temperature sensor for generating an output proportional to skin temperature of the individual.

3. The system of claim 1, further comprising a memory coupled to said processor,
   wherein said processor contains computer code, said code causes the outputs of said body fat, body water, weight sensors, and blood pressure unit to be recorded and stored in said memory and to be displayed by said portable display unit, and
   wherein, responsive to a user input, said code causes the outputs of said body fat, body water, weight sensors, and blood pressure unit to be retrieved from said memory and to be displayed by said portable display unit.

4. The system of claim 1, wherein said remote temperature unit further comprises a thermometer located outdoors for measuring the outdoor temperature, and wherein said second wireless transmitter is adapted to communicate with said portable display unit using radiofrequency wireless signals.

5. The system of claim 1, wherein said portable display unit is adapted to be in wireless communication with said first, second, and third transmitters using radiofrequency wireless signals.

6. The system of claim 1, wherein said portable display unit is adapted to display time.

* * * * *